United States Patent [19]

Giese et al.

[11] Patent Number: 5,747,338
[45] Date of Patent: May 5, 1998

[54] METHOD AND CONSTRUCT FOR SCREENING FOR INHIBITORS OF TRANSCRIPTIONAL ACTIVATION

[75] Inventors: Klaus Giese, Castro Valley; Jaime Escobedo, Alamo, both of Calif.

[73] Assignee: Chiron Corporation, Emeryville, Calif.

[21] Appl. No.: 719,577

[22] Filed: Sep. 25, 1996

Related U.S. Application Data

[63] Continuation of Ser. No. 689,926, Aug. 15, 1996.

[60] Provisional application No. 60/003,708, Sep. 13, 1995.

[51] Int. Cl.⁶ .................................................. C12N 5/10
[52] U.S. Cl. .................. 435/348; 435/367; 435/252.3; 435/254.21; 435/320.1; 536/24.5
[58] Field of Search .......................... 435/348, 367, 435/252.3, 252.33, 254.21, 320.1; 536/24.5

[56] References Cited

U.S. PATENT DOCUMENTS

| | | | |
|---|---|---|---|
| 5,464,758 | 11/1995 | Gossen et al. | 435/69.1 |
| 5,506,102 | 4/1996 | McDonnell | 435/6 |

FOREIGN PATENT DOCUMENTS

| | | |
|---|---|---|
| 653 438 | 8/1994 | European Pat. Off. . |
| WO91/16456 | 10/1991 | WIPO . |
| WO94/28124 | 12/1994 | WIPO . |
| WO95/09925 | 4/1995 | WIPO . |

OTHER PUBLICATIONS

Antoni et al, Adv. in Virus Res. 43:53–143 (1994).
Gaynor, AIDS 6:347–363 (1992).
Greenblatt et al, Nature 364: 401–406 (1993).
Hsu et al, Science 254: 1799–1802 (1991).
Hsu et al, Proc. Nat'l Acad. Sci. USA 90: 6395–6399 (1993).
Izant and Weintraub, Cell 36: 1007–1015 (1984).
Jones and Peterlin, Annu. Rev. Biochem. 63: 717–43 (1994).
Kao et al, Nature (London) 330: 489–493 (1987).
Mahshilkar et al, EMBO J. 14: 1542–1551 (1995).
Melton, PNAS USA 82: 144–148 (1985).
Selby et al, Genes Dev. 3: 547–558 (1989).
Sullenger, Cell 63: 601–608 (1990).
Volloch et al, Biochem. Biophyx. Res Commun. 179: 1600–1605 (1991).
Del Rosario et al, Nature Biotech. 14: 1592–1596 (1996).
Li et al, Cell 85: 319–329 (1996).
Wagner, Nature (London) 372: 333–335 (1994).
Holt et al., Antisense Res. Dev. 1(4):365–369 (1991).
Giovannangeli et al., Biochem USA 35/32/10539–10548 (1996).
Mountford et al., Proc. Nat'l Acad. Sci., 91(10):4303–4307 (1994).

*Primary Examiner*—James Ketter
*Attorney, Agent, or Firm*—Jane E.R. Potter; Robert P. Blackburn

[57] ABSTRACT

A collision construct is provided that contains a first regulatory sequence containing a first promoter linked to a reporter gene which is also linked to a second regulatory sequence containing a second promoter such that the reporter gene is under regulatory control of the first promoter. The direction of transcription under the first promoter is opposite the direction of transcription under the second promoter and activation of the second promoter interferes with reporter gene activity. The collision construct is used to screen inhibitors of the second regulatory sequence and the second promoter whereby a functional inhibitor causes an enhanced signal of the reporter gene. Vectors, host cells and kits containing the collision construct are provided, as well as methods for producing the collision construct, the vectors and host cells, and methods for screening candidate inhibitors for their ability to inhibit target promoter activities.

45 Claims, 5 Drawing Sheets

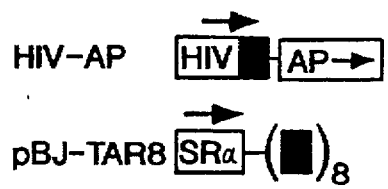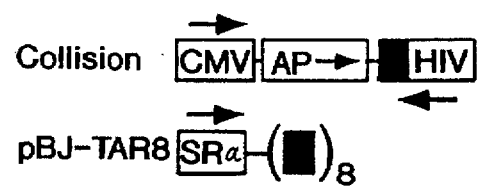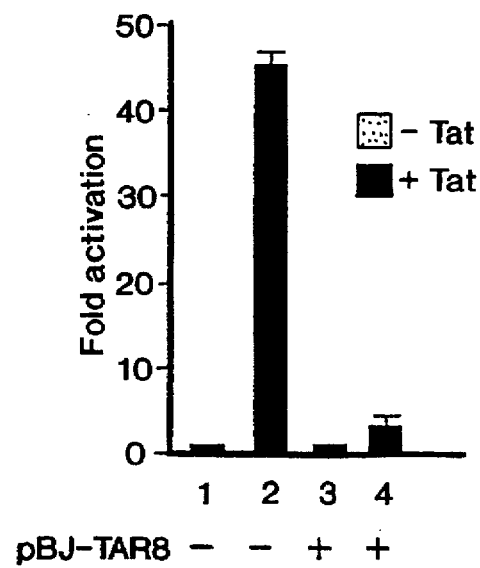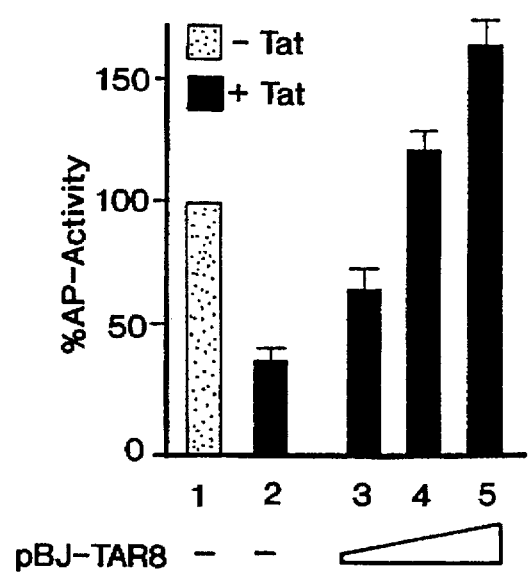
FIG. 5A
FIG. 5B

METHOD AND CONSTRUCT FOR SCREENING FOR INHIBITORS OF TRANSCRIPTIONAL ACTIVATION

CROSS-REFERENCE TO RELATED APPLICATION

This application is a continuation-in-part of U.S. Ser. No. 08/689,926, filed Aug. 15, 1996, which claims the benefit of U.S. provisional application Ser. No. 60/003,708, filed Sep. 13, 1995.

FIELD OF THE INVENTION

This invention relates to methods for screening and identifying inhibitors of promoters or inhibitors of transcriptional activation by use of a collision construct. The collision construct provides for increased expression of reporter gene signal in the presence of an appropriate inhibitor. This invention, thus, relates to the collision construct as well as methods for making and producing the collision construct, and to vectors, host cells and kits containing the collision construct.

BACKGROUND OF THE INVENTION

Past studies of inhibitors of gene function include studies of the inhibition of transcription of the gene, as described in Hsu et al, *Science* 254:1799–1802 (1991) and Hsu et al, *Proc. Nat'l Acad. Sci.* USA 90:6395–6399 (1993). Structural genes have a transcription regulatory region that contains one or more sequences, referred to herein as response elements, that are capable of binding to certain proteins, referred to herein as binding proteins, that activate or repress transcription or facilitate elongation of a mRNA transcript. These binding proteins include transcription factors, such as those described in Faisst & Meyer (1992), *Nucleic Acids Res.* 20:3–26; THE ENCYCLOPEDIA OF MOLECULAR BIOLOGY, J. Kendrew, ed. (Blackwell Science, Oxford (1994); and those that are identified in specialized data base, as described in Ghosh (1993), *Nucleic Acids Res.* 21:3117–3118.

A transcription factor, such as an activator, typically contains a domain that recognizes a specific DNA sequence, the response element, and binds it. Transcription activators may also contain another domain that interacts with other transcription factors to initiate transcription or to allow elongation of the RNA transcript. Thus, a molecule that inhibits binding of an activator to a response element, either by competitively binding to the DNA-binding domain of the activator or to the response element, or a molecule that blocks the transcription factor-interacting domain of the activator, would be expected to inhibit transcriptional activation.

Repressors, also mostly proteins, function in a similar manner, except that instead of activating transcription, the repressor binds to the response element, for example, an operator, and blocks transcription. Molecules that are capable of competitively binding to repressors activate transcription by removing the repressor from the response element. Thus, an inhibitor to the molecule that competitively binds to the repressor would be expected also to inhibit transcriptional activation.

There exist other modes of molecular action which also function to inhibit transcription and which operate by methods distinct from classic repression or activation of gene transcription described above. Such methods include, for example, catalytic events directed against the mRNA of a transcription factor. It would be desirable to employ these methods for inhibiting transcription of a target promoter or transcription of a transcription factor and to devise a method to screen for such inhibitors.

Conventionally, when researchers look for an inhibitor of a biological function, they look for a decrease in biological function or a decrease in a reporter signal that reflects inhibition of that function. Very often, a decrease in signal is difficult to interpret because the decrease may be the result of factors other than the presence of the supposed inhibitor being tested. For example, the decrease in signal may be caused by the presence of extraneous matter including toxic chemicals in the media, inappropriate incubation temperature, inappropriate incubation time, poor condition of the cells used in the test, etc. In order to resolve the matter, a number of time-consuming experiments have to be run with a number of controls.

It would be desirable, therefore, if the presence of an inhibitor can be reflected by an increase in reporter gene signal instead of a decrease.

SUMMARY OF THE INVENTION

It is, therefore, an object of the present invention, to provide a screening test for inhibitors that is capable of generating an increase in reporter signal in the presence of an inhibitor.

It is also an object of the present invention to provide for materials that can be used in such a screening test.

In accordance thereto, there is provided herein a construct, termed a collision construct, that contains a nucleic acid molecule, comprising a first regulatory sequence that comprises a first promoter, a reporter gene that is under transcriptional control of the first promoter, where the reporter gene is capable of providing a detectable signal upon transcription and translation thereof, and a second regulatory sequence that comprises a second promoter, where the direction of transcription under the first promoter is opposite to the direction of transcription under the second promoter, where regulation of transcription under the second promoter alters the reporter gene signal, and where the first promoter is different from the second promoter.

In accordance to a further object of the present invention, there is provided herein the collision construct as above, where the second promoter or the second regulatory sequence comprises a first response element that is capable of binding to a first binding protein to form a first binding pair, and the formation of the first binding pair regulates the activity of the second promoter.

In accordance with another object of the present invention, there is provided herein the collision construct as above, where the last nucleotide of the stop codon of the reporter gene is separated from the 3' terminus of the second promoter by a distance of about less than about 2050 nucleotides.

In accordance to still another object of the present invention, there is provided herein the collision construct as above, where one or both of the first promoter and second promoter are derived from a promoter or promoter/enhancer region of a gene selected from the group consisting of: a viral gene, a bacteriophage gene, a prokaryotic gene, and an eukaryotic gene. The eukaryotic gene can be a yeast or other fungal gene, an avian gene, an insect gene or a mammalian gene. Alternatively, the promoter or promoter/enhancer may be synthetically made, or partly derived and partly synthesized.

In accordance to yet another object of the present invention, there is provided herein the collision construct as above, where one or both of the first response element and the second response element, the latter optionally present in the first regulatory region, are derived from the regulatory sequence of a gene selected from the group consisting of: a viral gene, a bacteriophage gene, a prokaryotic gene, and an eukaryotic gene. The eukaryotic gene can be, for example, a yeast or other fungal gene, an insect gene, an avian gene, or a mammalian gene.

In accordance to a further object of the present invention, there is provided herein a method of using the collision construct as above for screening or identifying a candidate inhibitor for its ability to inhibit transcription under a target promoter, the method comprising the steps of providing a cell that contains the collision construct, where the second promoter in the construct is the target promoter and the cell is capable of expressing the collision construct to produce a reporter gene signal, determining reporter gene signal in the absence and presence of the candidate inhibitor, respectively, and comparing reporter gene signals obtained. An appropriate inhibitor is one that is capable of generating an increased reporter signal in the presence of an inhibitor.

In accordance to another object of the present invention, there is provided herein a method as above, where the second promoter or the second regulatory region in the collision construct comprises a response element that is capable of binding to a binding protein. The binding protein can be provided by coexpression in a cell of the collision construct and a vector that comprises a coding sequence for binding protein. Alternatively, the binding protein can be provided by a cell that produces it constitutively and the collision construct is then introduced into the cell. Also, the binding protein can be added directly to the cell that contains the collision construct.

In accordance to another object of the present invention, there is provided herein a method of making the collision construct by providing and linking together a first regulatory sequence that comprises a first promoter, a reporter gene that is capable of providing a detectable signal upon transcription and translation, a second regulatory sequence that comprises a second promoter, where the reporter gene is placed under regulatory control of the first promoter, the direction of transcription under the first promoter is opposite the direction of transcription of the second promoter, and the first promoter is different from the second promoter.

In accordance to a further object of the present invention, there is provided herein a method of production of the collision construct by culturing a host cell that comprises the collision construct, for example, a prokaryotic or eukaryotic host cell, for example, a bacterial or yeast cell.

In accordance with yet another object of the present invention, there is provided herein a kit that comprises the collision construct as above, or a vector or host cell containing the collision construct, with instructions for use thereof in accordance with the method described above.

BRIEF DESCRIPTION OF THE DRAWINGS

FIG. 2 shows that specific reduction of alkaline phosphatase expression in the presence of HIV-1 Tat protein is dependent on a functional TAR sequence in the LTR. When the collision construct #1152 was used, in the presence of inactive Tat plasmid, reporter gene signal was high. This signal was suppressed in the presence of active Tat plasmid by about 60%. When a portion of the TAR sequence was deleted (construct #1161), or when further portions of the promoter were deleted, there was no significant difference in reporter gene signal in the presence or absence of Tat. Thus, suppression of alkaline phosphatase expression in the collision construct is Tat protein and TAR sequence dependent.

FIG. 3 illustrates that HIV-1 promoter activation by Tat protein requires the presence of the TAR sequence and that TAR may possibly have a silencer function because when a portion of TAR was deleted, reporter gene signal in the absence of Tat increased as compared to that when the complete TAR sequence was present. Addition of Tat to cells containing this construct, #1166, which does not allow the formation of a TAR stem loop structure, enhanced reporter gene signal by about 2.5-fold. Additional deletion of the promoter region to include the TATA box and Sp1 binding sites resulted in complete loss of reporter gene signal, in the absence or presence of Tat.

FIG. 5 indicates that TAR decoys act as specific inhibitors of HIV-1 transcription. FIG. 5a shows inhibition of HIV-1 transcription in the presence of TAR decoys. At the top of FIG. 5a is a schematic diagram of an HIV-AP reporter gene construct and a plasmid expressing multimerized (8 copies) of transactivation response sequence, also called TAR decoys. The arrows indicate the direction of transcription and translation. The black boxes represent the TAR sequence. At the bottom of FIG. 5a, a schematic indicates that HeLa cells were transfected with various combinations of HIV-AP (1 µg) reporter and TAR expression plasmids (0.5 µg) in the presence or absence of 0.5 µg of Tat expression vector. AP activity was determined as described previously and is expressed as fold activation relative to the level obtained with the HIV-AP plasmid in the absence of Tat (represented in lane 1). FIG. 5b shows increased reporter gene expression in the collision construct by inhibition of HIV-1 promoter activity. At the top of FIG. 5b is a schematic representation of th collision construct and a plasmid expressing multimerized copies of the TAR sequence. At the bottom of FIG. 5b, HeLa cells were transfected with various combinations of the collision construct (1 μg) and increasing amounts of a TAR expression plasmid (lanes 3 to 5, 1 μg and 2 μg respectively) in the absence or presence of 0.5 μg Tat expression plasmid. The total DNA concentration in each experiment was kept constant by adding a Tat expression vector containing a premature stop codon and a pBJ plasmid expressing an unrelated (leptin) gene. Each column represents the mean of at least three independent experiments. Error bars represent standard error from multiple transfections.

DETAILED DESCRIPTION OF THE PREFERRED EMBODIMENTS

Figure 1:
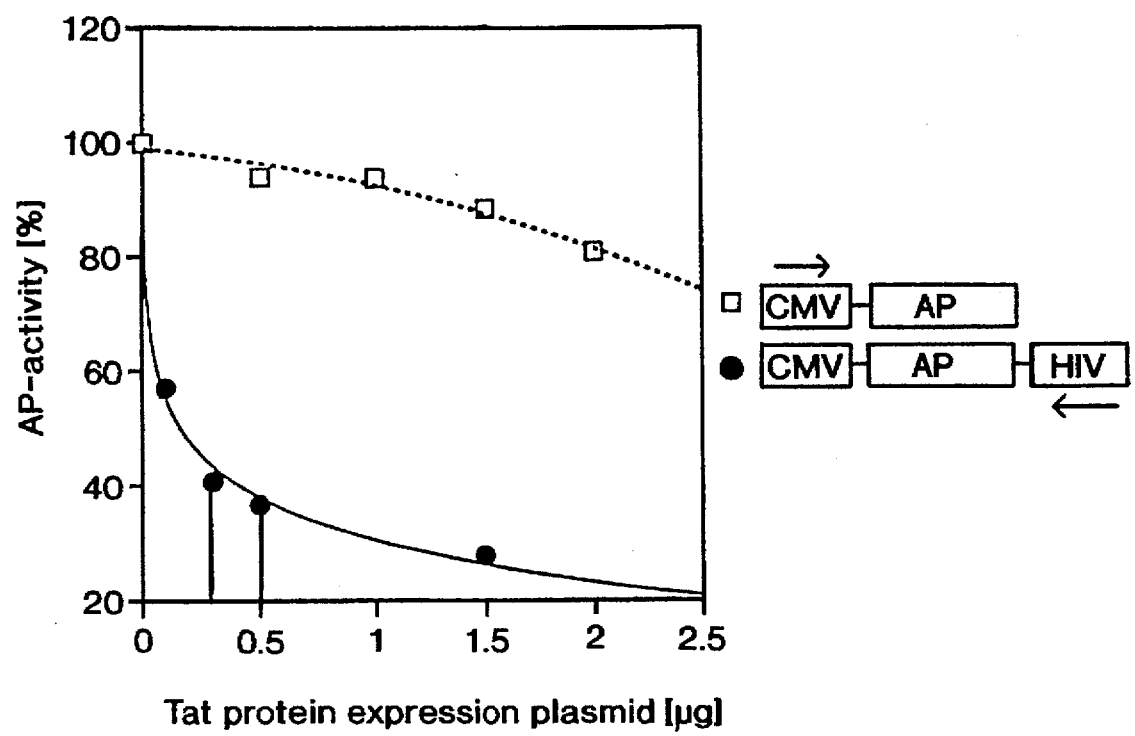
FIG. 1 is a schematic representation of a collision construct, transformed in HeLa cells, containing the CMV promoter and the HIV-1 promoter running in opposite directions and another construct for control in which the HIV-1 promoter was absent. The graph depicts Tat-dependent inhibition of CMV promoter activity over a range of Tat levels, in micrograms of Tat expression vector, from about 0 to 2. The symbol (●) represents the alkaline phosphatase gene expression in the collision construct. The symbol ○ represents alkaline phosphatase gene expression in the control construct showing nonspecific reduction of CMV promoter activity by Tat protein. Other abbreviations include AP, representing alkaline phosphatase; and CMV, representing the cytomegalovirus promoter/enhancer.

The invention described herein draws on previously published work and, at times, on pending patent applications. By way of example, such work consists of scientific papers, abstracts, or issued patents, and published patent applications. All published work cited herein are hereby incorporated by reference.

The inventors herein have discovered that a collision construct can be made that can be used for screening inhibitors of promoter or transcriptional activity. By use of this collision construct, the presence of a desired inhibitor is indicated by an enhancement in reporter gene signal.

Definitions

A "nucleic acid molecule", "nucleic acid sequence" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence or its complementary strand. A polynucleotide may include, for example, an antisense oligonucleotide, or a ribozyme, and may also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degredation. Synthetic nucleic acids can be ribozymes or antisense molecules, for example. Modifications to synthetic nucleic acid molecules include nucleic acid monomers or derivative or modifications thereof, including chemical moieties. For example, phosphothioates can be used for the modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis.

A "regulatory sequence" refers to a nucleic acid sequence encoding one or more elements that are capable of affecting or effecting expression of a gene sequence, including transcription or translation thereof, when the gene sequence is placed in such a position as to subject it to the control thereof. Such a regulatory sequence can be, for example, a minimal promoter sequence, a complete promoter sequence, an enhancer sequence, an upstream activation sequence ("UAS"), an operator sequence, a downstream termination sequence, a polyadenylation sequence, an optimal 5' leader sequence to optimize initiation of translation, and a Shine-Dalgarno sequence. Alternatively, the regulatory sequence can contain a combination enhancer/promoter element. The regulatory sequence that is appropriate for expression of the present construct differs depending upon the host system in which the construct is to be expressed. Selection of the appropriate regulatory sequences for use herein is within the capability of one skilled in the art. For example, in prokaryotes, such a regulatory sequence can include one or more of a promoter sequence, a ribosomal binding site, and a transcription termination sequence. In eukaryotes, for example, such a sequence can include one or more of a promoter sequence and/or a transcription termination sequence. If any necessary component of a regulatory sequence that is needed for expression is lacking in the collision construct, such a component can be supplied by a vector into which the collision construct can be inserted for transformation or reintroduction into a host cell. Regulatory sequences suitable for use herein may be derived from any source including a prokaryotic source, an eukaryotic source, a virus, a viral vector, a bacteriophage or a linear or circular plasmid. An example of a regulatory sequence is the human immunodeficiency virus ("HIV-1") promoter that is located in the U3 and R region of the HIV-1 long terminal repeat ("LTR"). Alternatively, the regulatory sequence herein can be a synthetic sequence, for example, one made by combining the UAS of one gene with the remainder of a requisite promoter from another gene, such as the GADP/ADH2 hybrid promoter.

A "minimal promoter" is a naturally occurring promoter that has been weakened so that it is not 100% active. For example, a promoter in which all but a TATA box has been deleted, such as the minimal fos promoter, as described in Berkowitz et al. (1989) Mol. Cell. Biol. 5:4272–4281.

A "reporter gene" refers to a nucleic acid molecule that encodes a polypeptide that is capable of providing a detectable signal either on its own upon transcription or translation or by reaction with another one or more reagents. Reporter genes suitable for use herein are conventional in the art, selection of which is within the capability of one skilled in the art. Examples of such reporter genes include that encoding the enzyme chloramphenicol acetyltransferase ("CAT"), the luc gene from the firefly that encodes luciferase, the bacterial lacZ gene from Escherichia coli that encodes β-galactosidase, alkaline phosphatase ("AP"), human growth hormone ("hGH"), the bacterial β-glucuronidase ("GUS"), and green fluorescent protein ("GFP"), as described in Ausubel et al., CURRENT PROTOCOLS IN MOLECULAR BIOLOGY (1994), (Greene Publishing Associates and John Wiley & Sons, New York, N.Y.).

A "response element" refers to a region of a nucleic acid molecule, usually, from a regulatory region of a gene, that is capable of specifically binding to a binding protein, such as an activator molecule, for activation of transcription or for allowing the elongation of a RNA transcript, or a repressor molecule, for inhibition of transcription. Some response elements are known in the art. Selection of a response element that is suitable for use herein is within the capability of one skilled in the art.

A "binding protein" herein refers to a protein that is capable of specifically binding to a response element for regulation of transcription. Some binding proteins are known. Selection of a binding protein suitable for use herein is also within the capability of one skilled in the art. A number of DNA binding proteins as well as response elements of the transcription regulatory regions are described in Wingender (1988), *Nucleic Acids Res.* 16:1879–1902; *Molecular Cell Biology*, J. Darnell, H. Lodish & D. Baltimore, (Scientific American Books, New York 1990); and Dhawale & Lane (1993), *Nucleic Acids Res.* 21:5537–5546. One example is the Tat/TAR combination found in viruses such as human immunodeficiency virus-1 ("HIV-1"), human immunodeficiency virus-2 ("HIV-2"), and simian immunodeficiency virus ("SIV"). In these viruses, trans-activator, "Tat", is the binding protein referred to herein and trans-activating response element, "TAR", is the response element referred to herein, as described in Jones & Peterlin (1994) *Ann Rev. Biochem.* (63:717–743; and Antoni et al. (1994), *Adv. Virus Res.* 43:53–145. Examples of response elements and binding proteins besides TAR and Tat include Rev response element ("RRE"), a NF-κB binding site, a Sp1 binding site, and Ga14 and LexA binding sites. Examples of binding proteins include Tat, Rev, NF-κB, Sp1, Ga14, and LexA.

The term "binding pair" refers to a pair of molecules, including a DNA/DNA pair, DNA/RNA pair, protein/DNA pair, protein/RNA pair, and a protein/protein pair in which the components of the pair bind specifically to each other with a higher affinity than to a random molecule, such that upon binding, the pair triggers a biological response, such as activation of transcription or where the binding protein is a repressor, suppresses a biological response, that is, transcription.

The term "specific binding" in reference to interaction between two molecules indicates a higher affinity binding and a lower dissociation constant than non-specific binding, thus, distinguishing specific binding from background binding.

The term "regulates," in the context of transcription, denotes both positive and negative regulation. Positive regulation is exemplified by activation. Negative regulation is exemplified by repression.

Although the methodology described below is believed to contain sufficient details to enable one skilled in the art to practice the present invention, other constructs not specifically exemplified, such as plasmids, can be constructed and purified using standard recombinant DNA techniques as described in, for example, Sambrook et al. (1989), MOLECULAR CLONING: A LABORATORY MANUAL, 2nd ed. (Cold Spring Harbor Press, Cold Spring Harbor, N.Y.); and under current regulations described in United States Department of HEW, NATIONAL INSTITUTE OF HEALTH (NIH) GUIDELINES FOR RECOMBINANT DNA RESEARCH.

In one embodiment of the present invention, therefore, the collision construct comprises a reporter gene coding sequence that is linked at its 5' end to a first regulatory sequence that comprises a first promoter such that the reporter gene is placed under transcriptional regulatory control of the first promoter. The reporter gene is linked at its 3' end to a second regulatory sequence that comprises a second promoter in such a fashion that transcriptional activity of the second promoter interferes with the transcriptional activity of the first promoter. This can be done, for example, by placing the first regulatory sequence and the second regulatory sequence in such a manner that transcription under the second promoter proceeds in a direction opposite to direction of transcription under the first promoter.

For uses in screening for inhibitors of transcriptional activation, a collision construct as described above is made with the promoter to be inhibited (hereafter "the target promoter") as the second promoter. The collision construct so made is inserted into a vector for expression, with or without the use of linker elements. The recombinant vector is then introduced into a compatible host cell that can effect the expression of the reporter gene. There are known vectors and host cells that can be used for these purposes, as described in greater detail below.

The regulatory sequences suitable for use herein can be any regulatory sequence that is compatible for use with the promoters for expression in a desired host cell. For example, if the collision construct contains a mammalian gene promoter, a regulatory sequence derived from mammalian systems would be desirable. The regulatory sequence can be a sequence naturally associated with the promoters selected for use herein, or can be a synthetic sequence, or partly synthetic or partly derived.

The promoters suitable for use herein can be any promoter, including those that are constitutively active or those that are inducible or regulatable. The promoters can be naturally derived or synthetically made. They can be derived from any genes, viral, prokaryotic or eukaryotic. The eukaryotic genes can be yeast or other fungal, insect, mammalian or avian genes. In a preferred embodiment, the target promoter is derived from a virus or a tumor cell. Examples of suitable promoters are described below in the portion relating to expression systems.

A suitable promoter for use as the first promoter in the present collision construct is one that possesses a transcriptional activity that is about the same strength as that of the second promoter. If the first promoter is comparatively much stronger than the second promoter, inhibition of reporter gene signal by the presence of the second or target promoter may be low, and an enhanced reporter gene signal in the presence of an inhibitor may be difficult to detect.

Thus, if an available promoter to be used in the collision construct as a first promoter is too strong, it may be desirable to weaken the promoter by deleting parts thereof to generate a minimal promoter. This can be done by a number of methods including, for example, restriction enzyme digestion. An example of a weakened promoter is one in which all but the TATA box is deleted. A promoter is considered too strong herein if it drives the expression of the reporter gene to about the same level regardless of the presence or absence of the second promoter that drives transcription in the opposite direction.

When the target promoter to be inhibited is constitutively active, a reporter gene signal expressed by a transformed host cell containing the collision construct can be first established in the absence of any inhibitors. A candidate inhibitor can then be introduced or added to the cells and the reporter gene expression can be monitored. Alternatively, the transformed cells containing the collision construct can be placed in a panel of microtiter wells and a panel of candidate inhibitors can be added to the cells, one inhibitor to each well. A suitable inhibitor is one that generates an enhanced reporter signal in its presence as compared with the signal produced in its absence.

The target promoter to be used herein includes promoters that are subject to regulation, such as activation, by the binding of a DNA-binding protein to a response element in the proximity of the target promoter. The response element can be naturally present in the target promoter or can be artificially linked to the target promoter. Thus, the present collision construct can be used to identify an inhibitor that can inhibit activation of the target promoter by inhibiting binding between the binding protein and the response element. This can be achieved by identifying an inhibitor that competitively binds either to the binding protein or to the response element. When the activity of the second promoter is inhibited, the reporter gene activity would return to a level similar to that in the absence of activation by the binding protein.

The binding protein can be introduced into the cells by addition thereof to the medium containing the cells and gently scraping the cells from the culture dish. Alternatively, the binding protein can be provided in the form of a vector containing the coding sequence of the binding protein and regulatory sequences that would allow expression thereof. The vector can be introduced into the host cell either at, before, or after introduction of the collision construct into the cell. In another embodiment of the present invention, stable cell lines containing a collision construct or the coding sequence of the binding protein can be first established, and the other sequence introduced later. Further alternatively, a stable cell line containing both the collision construct and the binding protein can be made and thereafter used for screening inhibitors.

The collision construct or vector containing the collision construct can be introduced into host cells by conventional techniques including electroporation, calcium phosphate treatment, and lipofectamine transfection. The target promoter can be a known promoter with a known nucleotide sequence that can be synthetically made or derived from a natural source such as a viral gene, a tumor cell gene or a fungal gene, for example. Typically, such promoters are excised from the natural source and inserted into the collision construct by use of restriction enzymes and/or linkers.

Alternatively, the sequence of the promoter may not be precisely known, but the general location of the promoter is known, for example, the promoter can be known to reside in a particular restriction fragment. In this instance, the restricted fragment can be used as the second regulatory sequence of the present collision construct.

In another embodiment of the present invention, it may be desirable to turn off the transcription of certain genes that are yet unidentified, for example, one responsible for production of a cancerous cell, even though the gene or genes responsible for this condition have not been identified. For this purpose, mRNA can be isolated from the tumor cell and compared to that obtained from normal cell by a common procedure known as subtractive hybridization. By substractive hybridization it can be determined which MRNA is present in the tumor cell but absent in normal cell. A cDNA molecule can be constructed based on the mRNA so obtained, and a fragment of the genomic DNA containing promoter activity can be isolated and used as a target promoter in the present collision. Although the invention is not limited to any theories of mechanism of how the invention works, the colliding promoter may generate antisense mRNA from the polynucleotide sequence 3' of the promoter which in turn can bind the another, endogenous copy of the gene and interfer with the transcription of that gene.

The collision construct herein can be inserted into a suitable vector for introduction into a host cell for expression and use thereof. A person skilled in the art would be able to select such a vector and host cell for such purposes. Moreover, examples of suitable vectors and host cells are described in greater detail below.

The reporter gene that is suitable for use herein can be any reporter gene that can be expressed in the desired host expression system, as described previously. For example, the reporter gene can be β-galactosidase, among others.

Similarly, the response element suitable for use herein can be any response element to which inhibition is desired. Examples of such response elements are as described above. The response element herein may be part of the promoter sequence by conventional techniques such as by synthesis of excision of a known sequence by restriction enzyme and linked to the promoter sequence with or without the use of linkers.

The DNA-binding proteins for use herein may be any binding protein as described above. Such binding proteins may be added to the cells containing the collision construct for use in screening inhibitors. In doing so, the cells can be scraped off the culture dish or well and mixed with the added binding protein.

Alternatively, the DNA-binding proteins can be introduced into the cell in the form of a vector containing the coding sequence of the binding protein and allowing the expression of the coding sequence. In this manner, a stable cell line containing the binding protein can be made and used for screening inhibitors. In another embodiment of the present invention, a cell that constitutively produces the binding protein constitutively can be used.

In a further embodiment of the present invention, a stable cell line containing the collision construct can be made. This can be done by introduction of the collision construct into a host cell, by conventional techniques such as electroporation, calcium phosphate treatment, and lipofectamine or transformation, and selecting a cell or cell line that stably expresses the collision construct.

A candidate inhibitor to be tested for its inhibitory activity on a target promoter, or on transcriptional activity can be added to a cell harboring the collision construct in which the target promoter is the second promoter of the construct, and optimally, is desired, providing the cell also with a binding protein. Expression of reporter gene signal is observed and compared in the absence and in the presence of the candidate inhibitor, respectively.

Besides testing a single candidate inhibitor, stably transformed cell lines containing the collision construct and optionally containing a vector containing the coding sequence of a binding protein can be placed in microtiter wells and a panel of inhibitors is added thereto. Reporter gene signals are also observed and compared in the absence and presence of the candidate inhibitors, respectively.

In a further embodiment of the present invention, a method is provided for screening inhibitors, such as, for example, inhibitors to promoters and transcriptional activators. Promoters that can be used for screening inhibitors and used in the collision construct can be any desired promoters including, for example, promoters from viruses and cancer cells, bacteria and fungi. Transcriptional activators that can be inhibited can be any desired transcriptional activator including, for example, Tat, Rev, NFκB and Sp1. The region of the promoter that can be inhibited herein can be any region that binds transcription factors including, for example, TAR, RRE (Rev response element), NFκB binding site and Sp1 binding site.

An embodiment of the present invention can be tailored to screen in vivo in cells a random library of ribozymes for those ribozymes which act as inhibitors of transcription. Ribozymes may act by catalytically interrupting transcription by targeting an RNA molecule of a transcription factor that interacts with the promoter or by targeting the MRNA of a reporter gene. However, the use of the invention for screening ribozyme libraries is not limited to any theory of ribozyme function. Unlike inhibitors of transcription which inhibit the promoter by interfering with a promoter-transcription factor interaction, a DNA-protein interaction, ribozymes catalytically disable an RNA molecule. In the context of the present invention, ribozymes which inhibit the second promoter in the collision construct can be selected from random synthetically derived ribozyme libraries by enhanced reporter gene signal, indicating that a ribozyme is acting to disable the second promoter, or the MRNA for a transcription factor that interacts with that promoter.

In one embodiment of the present invention, the subunits of a collision construct, including a first regulatory sequence, a reporter gene, optionally, a response element or elements, and a second regulatory sequence, can all be obtained from known sources using conventional techniques of restriction enzyme digestion to remove these elements from such sources. Alternatively, these subunits can be made synthetically by chemical synthesis or semi-synthetically by isolating parts thereof from known sources and either combining them or by combining them and making any missing parts synthetically. Once obtained or made, these subunits can be linked together, for example, by use of known linker sequences, so as to place the reporter gene under regulatory control of the first regulatory sequence, with the direction of transcription going in one direction, 5' to 3' and the second regulatory sequence under regulatory control of the response element, with the direction of transcription by the second regulatory sequence running in a direction, 5' to 3', but opposite that of the first regulatory sequence. Placement of the response element and the second regulatory sequence is such that activation of transcription of the second regulatory sequence reduces the reporter gene signal upon transcription and translation thereof, presumably as a result of collision between the two transcription units. A mechanism by which the second regulatory sequence generates an anti-sense message that blocks translation of the reporter gene cannot be ruled out.

The spacing between the reporter gene and the response element can be varied to attain the desired level of inhibition of reporter gene activity. In one embodiment of the present invention, the spacing between the 3' end of the reporter gene and the +1 nucleotide of the promoter of the second regulatory sequence is less than 2200 nucleotides. Preferably, this spacing is less than 1000 nucleotides; more preferably, it is less than 800 nucleotides. Most preferably, the spacing is between about 600 nucleotides and about 20 nucleotides. In particular, spacings of about 21, 94, 153, 406, and 556 base pairs are preferred. In an alternative embodiment, the target or second promoter of the collision construct can be optimally placed at a distance of up to 1500 base pairs from the 3' terminus of the first promoter. Thus, a reporter gene is selected that comprises a sequence that is shorter than or the same as this optimal distance.

The first response element can also be linked to the second regulatory sequence using linker sequences or the combined first response element and second regulatory sequence can be removed from a known source, again by restriction enzyme digestion.

The response element will usually be placed at the 5' terminus of the second regulatory region, in accordance with the nature of most promoters which would comprise the second regulatory regions of this invention. However, for example, when the second regulatory region is comprised of a promoter for which it is appropriate to place the response element at the 3' terminus, the response element will be most appropriately placed at the 3' terminus. Preferably, this response element is placed at its natural position in juxtaposition to the promoter being used. For example, when the HIV-1 LTR promoter is used, the response element, TAR, is situated 3' to the +1 nucleotide of the promoter. In other primate immunodeficiency viruses and in a subset of related nonprimate lentiviruses, the response element will also be most appropriately positioned at the 3' terminus of the second regulatory region. See for example a discussion of the characteristics of the promoters of such viruses in Cullen, *Cell* (1993) 73:417–420. The response element herein can also be multimerized to produce a more dramatic effect. An example of a response element that has been multimerized is the [tet-op]$_7$ which is an operator responsive to tetracycline induction.

Once made, the collision construct can be introduced into an appropriate host cell for expressions thereof, including prokaryotic system such as bacterial, or eukaryotic system, such as yeast, insect cell system, or mammalian system, such as those described below. The binding protein may also be expressed in the expression systems described below.

Expression in Bacterial Cells

Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the β-lactamase (bla) promoter system, bacteriophage λPL, and T7. In addition, synthetic promoters can be used, such as the tac promoter. The β-lactamase and lactose promoter systems are described in Chang et al., *Nature* (1978) 275:615, and Goeddel et al., *Nature* (1979) 281:544; the alkaline phosphatase, tryptophan (trp) promoter system are described in Goeddel et al., *Nucleic Acids Res.* (1980) 8:4057 and EP 36,776 and hybrid promoters such as the tac promoter is described in U.S. Pat. No. 4,551,433 and de Boer et al., *Proc. Natl. Acad. Sci. USA* (1983) 80:21–25. However, other known bacterial promoters useful for expression of eukaryotic proteins are also suitable. A person skilled in the art would be able to operably ligate such promoters to the coding sequences of interest, for example, as described in Siebenlist et al., *Cell* (1980) 20:269, using linkers or adaptors to supply any required restriction sites. Promoters for use in bacterial systems also generally will contain a Shine-Dalgarno (SD) sequence operably linked to the DNA encoding the target polypeptide. For prokaryotic host cells that do not recognize and process the native target polypeptide signal sequence, the signal sequence can be substituted by a prokaryotic signal sequence selected, for example, from the group of the alkaline phosphatase, penicillinase, Ipp, or heat stable enterotoxin II leaders. The origin of replication from the plasmid pBR322 is suitable for most Gram-negative bacteria.

The foregoing systems are particularly compatible with *Escherichia coli*. However, numerous other systems for use in bacterial hosts including Gram-negative or Gram-positive organisms such as *Bacillus spp.*, *Streptococcus spp.*, *Streptomyces spp.*, *Pseudomonas* species such as *P. aeruginosa*, *Salmonella typhimurium*, or *Serratia marcescans*, among others. Methods for introducing exogenous DNA into these hosts typically include the use of CaCl$_2$ or other agents, such as divalent cations and DMSO. DNA can also be introduced into bacterial cells by electroporation, nuclear injection, or protoplast fusion as described generally in Sambrook et al. (1989), MOLECULAR CLONING: A LABORATORY MANUAL, 2d edition (Cold Spring Harbor Press, Cold Spring Harbor, N.Y.). These examples are illustrative rather than limiting. Preferably, the host cell should secrete minimal amounts of proteolytic enzymes. Alternatively, in vitro methods of cloning, e.g., PCR or other nucleic acid polymerase reactions, are suitable.

Prokaryotic cells used in this invention are cultured in suitable media, as described generally in Sambrook et al. (1989), MOLECULAR CLONING: A LABORATORY MANUAL, 2d edition (Cold Spring Harbor Press, Cold Spring Harbor, N.Y.).

Expression in Yeast Cells

Expression and transformation vectors, either extrachromosomal replicons or integrating vectors, have been developed for transformation into many yeasts. For example, expression vectors have been developed for, among others, the following yeasts: Saccharomyces cerevisiae, as described in Hinnen et al., Proc. Natl. Acad. Sci. USA (1978) 75:1929; Ito et al., J. Bacteriol. (1983) 153:163; Candida albicans as described in Kurtz et al., Mol. Cell. Biol. (1986) 6:142; Candida maltose, as described in Kunze et al., J. Basic Microbiol. (1985) 25:141; Hansenula polymorpha, as described in Gleeson et al., J. Gen. Microbiol. (1986) 132:3459 and Roggenkamp et al., Mol. Gen. Genet. (1986) 202:302); Kluyveromyces fragilis, as described in Das et al., J. Bacteriol. (1984) 158:1165; Kluyveromyces lactis, as described in De Louvencourt et al., J. Bacteriol. (1983) 154:737 and Van den Berg et al., Bio/Technology (1990) 8:135; Pichia guillerimondii, as described in Kunze et al., J. Basic Microbiol. (1985) 25:141; Pichia pastoris, as described in Cregg et al., Mol. Cell. Biol. (1985) 5:3376 and U.S. Pat. Nos. 4,837,148 and 4,929,555; Schizosaccharomyces pombe, as described in Beach and Nurse, Nature (1981) 300:706; and Yarrowia lipolytica, as described in Davidow et al., Curr. Genet. (1985) 10:380 and Gaillardin et al., Curr. Genet. (1985) 10:49, Aspergillus hosts such as A. nidulans, as described in Ballance et al., Biochem. Biophys. Res. Commun. (1983) 112:284–289; Tilburn et al., Gene (1983) 26:205–221 and Yelton et al., Proc. Natl Acad. Sci. USA (1984) 81:1470–1474, and A. niger, as described in Kelly and Hynes, EMBO J. (1985) 4:475479; Trichoderma reesia, as described in EP 0 244 234, and filamentous fungi such as, e.g, Neurospora, Penicillium, Tolypocladium, as described in WO 91/00357.

Control sequences for yeast vectors are known and include promoters regions from genes such as alcohol dehydrogenase (ADH), as described in EP 0 284 044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 0 329 203. The yeast PHO5 gene, encoding acid phosphatase, also provides useful promoter sequences, as described in Myanohara et al., Proc. Natl. Acad. Sci. USA (1983) 80:1. Other suitable promoter sequences for use with yeast hosts include the promoters for 3-phosphoglycerate kinase, as described in Hitzeman et al., J. Biol. Chem. (1980) 255:2073, or other glycolytic enzymes, such as pyruvate decarboxylase, triosephosphate isomerase, and phosphoglucose isomerase, as described in Hess et al, J. Adv. Enzyme Reg. (1968) 7:149 and Holland et al., Biochemistry (1978) 17:4900. Inducible yeast promoters having the additional advantage of transcription controlled by growth conditions, include those from the list above and others including the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 0 073 657. Yeast enhancers also are advantageously used with yeast promoters. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region, as described in U.S. Pat. Nos. 4,876,197 and 4,880,734. Other examples of hybrid promoters include promoters which consist of the regulatory sequences of either the ADH2, GAL4, GAL10, or PHO5 genes, combined with the transcriptional activation region of a glycolytic enzyme gene such as GAP or PYK, as described in EP 0 164 556. Furthermore, a yeast promoter can include naturally occurring promoters of non-yeast origin that have the ability to bind yeast RNA polymerase and initiate transcription.

Other control elements which may be included in the yeast expression vectors are terminators, for example, from GAPDH and from the enolase gene, as described in Holland et al., J. Biol. Chem. (1981) 256:1385, and leader sequences which encode signal sequences for secretion. DNA encoding suitable signal sequences can be derived from genes for secreted yeast proteins, such as the yeast invertase gene as described in EP 0 012 873 and JP 62,096,086 and the α-factor gene, as described in U.S. Pat. Nos. 4,588,684, 4,546,083 and 4,870,008 and EP 0 324 274 and WO 89/02463. Alternatively, leaders of non-yeast origin, such as an interferon leader, also provide for secretion in yeast, as described in EP 0 060 057.

Methods of introducing exogenous DNA into yeast hosts are well known in the art, and typically include either the transformation of spheroplasts or of intact yeast cells treated with alkali cations. Transformations into yeast can be carried out according to the method described in Van Solingen et al., J Bact. (1977) 130:946 and Hsiao et al., Proc. Natl. Acad. Sci. USA (1979) 76:3829. However, other methods for introducing DNA into cells such as by nuclear injection, electroporation, or protoplast fusion may also be used as described generally in Sambrook et al., cited above.

For yeast secretion the native target polypeptide signal sequence may be substituted by the yeast invertase, α-factor, or acid phosphatase leaders. The origin of replication from the 2 μ plasmid origin is suitable for yeast. A suitable selection gene for use in yeast is the trp1 gene present in the yeast plasmid described in Kingsman et al., Gene (1979) 7:141 or Tschemper et al., Gene (1980) 10:157. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

For intracellular production of the present polypeptides in yeast, a sequence encoding a yeast protein can be linked to a coding sequence of the desired polypeptide to produce a fusion protein that can be cleaved intracellularly by the yeast cells upon expression. An example, of such a yeast leader sequence is the yeast ubiquitin gene.

Expression in Insect Cells

Baculovirus expression vectors (BEVs) are recombinant insect viruses in which the coding sequence for a foreign gene to be expressed is inserted behind a baculovirus promoter in place of a viral gene, e.g., polyhedrin, as described in Smith and Summers, U.S. Pat. No. 4,745,051.

An expression construct herein includes a DNA vector useful as an intermediate for the infection or transformation of an insect cell system, the vector generally containing DNA coding for a baculovirus transcriptional promoter, optionally but preferably, followed downstream by an insect signal DNA sequence capable of directing secretion of a desired protein, and a site for insertion of the foreign gene encoding the foreign protein, the signal DNA sequence and the foreign gene being placed under the transcriptional control of a baculovirus promoter, the foreign gene herein being the coding sequence of the desired polypeptide.

The promoter for use herein can be a baculovirus transcriptional promoter region derived from any of the over 500 baculoviruses generally infecting insects, such as, for example, the Orders Lepidoptera, Diptera, Orthoptera, Coleoptera and Hymenoptera including, for example, but not limited to the viral DNAs of *Autographo californica* MNPV, *Bombyx mori* NPV, *rrichoplusia ni* MNPV, *Rachlplusia ou* MNPV or *Galleria mellonella* MNPV, *Aedes aegypti*, *Drosophila melanogaster*, *Spodoptera frugiperda*, and *Trichoplusia ni*. Thus, the baculovirus transcriptional promoter can be, for example, a baculovirus immediate-early gene IEI or IEN promoter; an immediate-early gene in combination with a baculovirus delayed-early gene promoter region selected from the group consisting of a 39K and a HindIII fragment containing a delayed-early gene; or a baculovirus late gene promoter. The immediate-early or delayed-early promoters can be enhanced with transcriptional enhancer elements.

Particularly suitable for use herein is the strong polyhedrin promoter of the baculovirus, which directs a high level of expression of a DNA insert, as described in Friesen et al. (1986) "The Regulation of Baculovirus Gene Expression" in: THE MOLECULAR BIOLOGY OF BACULOVIRUSES (W. Doerfler, ed.); EP 0 127 839 and EP 0 155 476; and the promoter from the gene encoding the p10 protein, as described in Vlak et al., *J. Gen. Virol.* (1988) 69:765–776.

The plasmid for use herein usually also contains the polyhedrin polyadenylation signal, as described in Miller et al., *Ann. Rev. Microbiol.* (1988) 42:177 and a procaryotic ampicillin-resistance (amp) gene and an origin of replication for selection and propagation in *E. coli*. DNA encoding suitable signal sequences can also be included and is generally derived from genes for secreted insect or baculovirus proteins, such as the baculovirus polyhedrin gene, as described in Carbonell et al., *Gene* (1988) 73:409, as well as mammalian signal sequences such as those derived from genes encoding human α-interferon as described in Maeda et al., *Nature* (1985) 315:592–594; human gastrin-releasing peptide, as described in Lebacq-Verheyden et al., *Mol. Cell. Biol.* (1988) 8:3129; human IL-2, as described in Smith et al., *Proc. Natl. Acad. Sci. USA* (1985) 82:8404; mouse IL-3, as described in Miyajima et al., *Gene* (1987) 58:273; and human glucocerebrosidase, as described in Martin et al., *DNA* (1988) 7:99.

Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified and can be used herein. See, for example, the description in Luckow et al., *Bio/Technology*(1988) 6:47–55, Miller et al., in GENETIC ENGINEERING (Setlow, J. K. et al. eds.), Vol. 8 (Plenum Publishing, 1986), pp. 277–279, and Maeda et al., *Nature*, (1985) 315:592–594. A variety of such viral strains are publicly available, e.g., the L-1 variant of *Autographa californica* NPV and the Bm-5 strain of *Bombyx mori* NPV. Such viruses may be used as the virus for transfection of host cells such as *Spodoptera frugiperda* cells.

Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well defined component of this regulatory cascade is IEI, a preferred immediate-early gene of *Autographo californica* nuclear polyhedrosis virus (AcMNPV). IEI is expressed in the absence of other viral functions and encodes a product that stimulates the transcription of several genes of the delayed-early class, including the preferred 39K gene, as described in Guarino and Summers, *J. Virol.* (1986) 57:563–571 and *J. Virol.* (1987) 61:2091–2099 as well as late genes, as described in Guarino and Summers, *Virol.* (1988) 162:444–451.

Immediate-early genes as described above can be used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII fragment of the baculovirus genome. In the present instance, the 39K promoter region can be linked to the foreign gene to be expressed such that expression can be further controlled by the presence of IEI, as described in L. A. Guarino and Summers (1986a), cited above; Guarino & Summers (1986b) *J. Virol.*, (1986) 60:215–223, and Guarino et al. (1986c), *J. Virol.* (1986) 60:224–229.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. For example, the hr5 enhancer sequence can be linked directly, in cis, to the delayed-early gene promoter region, 39K, thereby enhancing the expression of the cloned heterologous DNA as described in Guarino and Summers (1986a), (1986b), and Guarino et al. (1986).

The polyhedrin gene is classified as a very late gene. Therefore, transcription from the polyhedrin promoter requires the previous expression of an unknown, but probably large number of other viral and cellular gene products. Because of this delayed expression of the polyhedrin promoter, state-of-the-art BEVs, such as the exemplary BEV system described by Smith and Summers in, for example, U.S. Pat. No., 4,745,051 will express foreign genes only as a result of gene expression from the rest of the viral genome, and only after the viral infection is well underway. This represents a limitation to the use of existing BEVs. The ability of the host cell to process newly synthesized proteins decreases as the baculovirus infection progresses. Thus, gene expression from the polyhedrin promoter occurs at a time when the host cell's ability to process newly synthesized proteins is potentially diminished for certain proteins. As a consequence, the expression of secretory glycoproteins in BEV systems is complicated due to incomplete secretion of the cloned gene product, thereby trapping the cloned gene product within the cell in an incompletely processed form.

While it has been recognized that an insect signal sequence can be used to express a foreign protein that can be cleaved to produce a mature protein, the present invention is preferably practiced with a mammalian signal sequence.

An exemplary insect signal sequence suitable herein is the sequence encoding for a Lepidopteran adipokinetic hormone (AKH) peptide. The AKH family consists of short blocked neuropeptides that regulate energy substrate mobilization and metabolism in insects. In a preferred embodiment, a DNA sequence coding for a Lepidopteran *Manduca sexta* AKH signal peptide can be used. Other insect AKH signal peptides, such as those from the Orthoptera *Schistocerca gregaria* locus can also be employed to advantage. Another exemplary insect signal sequence is the sequence coding for Drosophila cuticle proteins such as CP1, CP2, CP3 or CP4.

Currently, the most commonly used transfer vector that can be used herein for introducing foreign genes into AcNPV is pAc373. Many other vectors, known to those of skill in the art, can also be used herein. Materials and methods for baculovirus/insect cell expression systems are commercially available in a kit form from companies such as Invitrogen (San Diego Calif.) ("MaxBac" kit). The techniques utilized herein are generally known to those skilled in the art and are fully described in Summers and Smith, A MANUAL OF METHODS FOR BACULOVIRUS VECTORS AND INSECT CELL CULTURE PROCEDURES, Texas Agricultural Experiment Station Bulletin No. 1555, Texas A & M University (1987); Smith et al., *Mol. Cell. Biol.* (1983) 3:2156, and Luckow and Summers (1989). These include, for example, the use of pVL985 which alters the polyhedrin start codon from ATG to ATT, and which introduces a BamHI cloning site 32 base pairs downstream from the ATT, as described in Luckow and Summers, *Virology* (1989) 17:31.

Thus, for example, for insect cell expression of the present polypeptides, the desired DNA sequence can be inserted into the transfer vector, using known techniques. An insect cell host can be cotransformed with the transfer vector containing the inserted desired DNA together with the genomic DNA of wild type baculovirus, usually by cotransfection. The vector and viral genome are allowed to recombine resulting in a recombinant virus that can be easily identified and purified. The packaged recombinant virus can be used to infect insect host cells to express the desired polypeptide.

Other methods that are applicable herein are the standard methods of insect cell culture, cotransfection and preparation of plasmids are set forth in Summers and Smith (1987), cited above. This reference also pertains to the standard methods of cloning genes into AcMNPV transfer vectors, plasmid DNA isolation, transferring genes into the AcmMNPV genome, viral DNA purification, radiolabeling recombinant proteins and preparation of insect cell culture media. The procedure for the cultivation of viruses and cells are described in Volkman and Summers, *J. Virol.* (1975) 19:820–832 and Volkman, et al., *J. Virol.* (1976) 19:820–832.

EXPRESSION IN MAMMALIAN CELLS

The polypeptides of the present invention can be expressed in mammalian cells, such as HeLa cells, using promoters and enhancers that are functional in those cells. Synthetic non-natural promoters or hybrid promoters can also be used herein. For example, a T7T7/T7 gene promoter can be constructed and used, in accordance with Chen et al., *Nucleic Acids Res.* 22:2114–2120 (1994), where the T7 polymerase is under the regulatory control of its own promoter and drives the transcription of the inserted coding sequence, which is placed under the control of another T7 promoter. Also suitable for use herein is the gene for the CCAAT/enhancer-binding protein C/EBPα, as described in Birkenmeier et al., *Genes Dev.* (1989) 3:1146–1156.

Typical promoters for mammalian cell expression include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Preferably a sequence for optimization of initiation of translation, located 5' to the polypeptide coding sequence, is also present. Examples of transcription terminator/polyadenylation signals include those derived from SV40, as described in Sambrook et al. (1989), cited previously. Introns, containing splice donor and acceptor sites, may also be designed into the constructs of the present invention.

Enhancer elements can also be used herein to increase expression levels of the mammalian constructs. Examples include the SV40 early gene enhancer, as described in Dijkema et al., *EMBO J.* (1985) 4:761 and the enhancer/promoter derived from the long terminal repeat (LTR) of the Rous Sarcoma Virus, as described in Gorman et al., *Proc. Natl. Acad. Sci. USA* (1982*b*) 79:6777 and human cytomegalovirus, as described in Boshart et al., *Cell* (1985) 41:521. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

There exist expression vectors that provide for the transient expression in mammalian cells of DNA encoding the target polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful for purposes of identifying analogs and variants of the target polypeptide that have target polypeptide-like activity.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. General aspects of mammalian cell host system transformations have been described by Axel in U.S. Pat. No. 4,399,216.

Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, as well as others.

The mammalian host cells used to produce the target polypeptide of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM1], Sigma) are suitable for culturing the host cells. In addition, any of the media described in Ham and Wallace, Meth. Enz. (1979) 58:44, Barnes and Sato, Anal. Biochem. (1980) 102:255, U.S. Pat. Nos. 4,767,704, 4,657,866, 4,927,762, or 4,560,655, WO 90/103430, WO 87/00195, and U.S. RE 30,985, may be used as culture media for the host cells. Any of these media may be supplemented as necessary with hormones and/or other growth factors such as insulin, transferrin, or epidermal growth factor, salts (such as sodium chloride, calcium, magnesium, and phosphate), buffers (such as HEPES), nucleosides (such as adenosine and thymidine), antibiotics (such as Gentamycin™ M drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The collision construct can be introduced into host cells by conventional techniques including lipofectamine, DEAE-dextran, electroporation, and calcium phosphate, and as described above.

For use for in screening inhibitors, a stable cell line that contains the collision construct can be made and selected. For example, the collision construct is electroporated together with a selectable marker gene, for example neomycin. G418 resistant colonies are assayed for the existence and functionality of the collision construct. The cell line can be prokaryotic or eukaryotic in origin. Preferably, the cell line is eukaryotic, more preferably, mammalian. In a preferred embodiment, the cell line can be derived from HeLa cells, T-cells, B-cells and 293 cells.

The stable cell line containing the collision construct can also be cotransfected with a plasmid containing a binding protein. The coding sequence for the binding protein can be inserted into an expression plasmid, such as pCG, a pEVRF derivative, described in Giese et al., *Genes & Development* (1995) 9:995–1008. pEVRF is described in Matthias et al., *Nucleic Acids Res.* (1989) 17:6418. pCG has a modified polylinker, and directs expression in mammalian cells from the human cytomegalovirus promoter/enhancer region. The coding sequence for the binding protein can also be inserted into the expression plasmid pCDNA (Clontech, Palo Alto, Calif.). The DNA construct encoding the binding protein can be made by standard methods of recombinant DNA technology as described in Sambrook et al. (1989) MOLECULAR CLONING: A LABORATORY MANUAL, 2nd ed. (Cold Spring Harbor Press, Cold Spring Harbor, N.Y.) and Ausubel et al., cited previously.

Alternatively, the collision construct can be transfected into a cell line that constitutively expresses a binding protein, such as, for example, HeLa cells, T-cells, B-cells or 293 cells that have been stably transfected with a vector that directs expression of the binding protein.

Further alternatively, the host cell carrying the collision construct for use in screening can be exposed to a binding protein that is added into the medium containing the transfected cells. In a preferred embodiment, a Tat protein expression vector is added to a cell line carrying the collision construct. The amount of the expression vector can be varied depending upon the extent of inhibition of reporter gene activity desired. It is desirable to work in the range of about 50% to 90% AP activity, preferably 60% to 80% AP activity in the absence of activation of the second regulatory sequence and in the range of about 10% to 50%, preferably 20% to 40% AP activity, in the presence of activation of the second regulatory sequence.

Thus, in using the host cell that contains the collision construct for screening inhibitors, the reporter gene activity is determined in the absence of the binding protein, in the presence of the binding protein, and in the presence of candidate inhibitors being screened. A candidate that increases reporter gene activity in the presence of a binding protein that activates transcription, for example, can be selected and further tested as an inhibitor to transcriptional activation.

In another embodiment of the present invention, kits can be made that contain the present collision construct for screening for inhibitors of transcriptional activation. Such kits can include vectors or host cells containing one or more of the present collision constructs in suitable containers, along with the reagents and materials required for the conduct of the assay or descriptions of those remaining reagents necessary, as well as a suitable set of assay instructions. Other materials or reagents can include, for example, diluents, buffers, host cells and other reagents, appropriate containers such as tubes, plates, etc., and may be included in the kit, or described in the instructions.

The present invention will now be illustrated by reference to the following examples which set forth particularly advantageous embodiments. However, it should be noted that these embodiments are illustrative and are not to be construed as restricting the invention in any way. In particular, other promoters or response elements and other reporter gene can be substituted for the ones described herein. Further objects, features, and advantages of the present invention will become apparent from the following examples. It should be understood, however, that the examples are given by way of illustration only, since various changes and modifications within the spirit and scope of the invention will become apparent to those skilled in the art from this detailed description.

EXAMPLE 1

Construction of the Collision Construct with CMV and HIV-1 Promoters and an Alkaline Phosphatase Reporter Gene: Construct #1152

In one embodiment of the present invention, the collision construct containing the human cytomegalovirus ("hCMV") promoter, the gene for the secreted form of the human placental heat-stable alkaline phosphatase ("AP") and the promoter of the human immunodeficiency virus-i ("HIV-1"), was generated from precursor constructs as described below.

A nucleotide sequence comprising the hCMV promoter and a region derived from the herpes simplex thymidine kinase, tk, gene for the optimal initiation of translation (hereafter "the tk upstream region"), was isolated from plasmid pCG. Plasmid pCG, described in Giese et al., *Genes and Development* (1995) 9:995–1008, is a pEVRF derivative, as described in Matthias et al., cited previously. pCG has a modified polylinker, and directs expression in mammalian cells from the human cytomegalovirus promoter/enhancer region. The hCMV promoter was isolated from pCG by digestion with restriction enzymes EcoRi and XbaI (Boehringer Mannheim, Germany). Restriction digestion for purposes herein was conducted essentially as described in Sambrook et al., cited previously, and Ausubel et al., cited previously, or in accordance with the manufacturer's recommendations. For example, digestions were typically conducted using 2 µl of 10× restriction buffer, 0.1 to 4 µg of DNA in water or TE buffer, 1–5 U of enzyme per µg of DNA and water to obtain a total volume of 20 µl. The components of the digest were incubated at 37° C. from about 10 minutes to overnight, depending on the amount of DNA being digested.

The hCMV promoter sequence isolated from pCG was then ligated into plasmid pTZ19U, purchased from Pharmacia (Piscataway, N.J.), that had been cleaved with the same restriction enzymes, EcoRI and XbaI. The resulting plasmid was designated construct #1080. Ligation reactions herein were essentially performed as directed by the manufacturer of the ligase (Boehringer Mannheim, Germany) and along the principles described in Sambrook et al., cited previously, and Ausubel et al., cited previously. Briefly, approximately 10 to 100 fempto moles ($10^{-15}$) of vector DNA were ligated with 3 to 10 fold molar excess of insert DNA in a final volume of 20 µl using T4 DNA ligase (Boehringer Mannheim, Germany) at 16° C. from about 10 minutes to overnight, depending on the amount of DNA being ligated.

The coding region of the alkaline phosphatase gene was isolated from plasmid pSEAP-Basic, purchased from Clontech (Palo Alto, Calif.) by restriction with HindIII and SalI and ligated into plasmid Bluescript, purchased from Stratagene (La Jolla, Calif.) that had been cleaved with the same enzymes. The resulting plasmid, designated construct #1067, was cleaved with ClaI and SalI, the 5'-overhangs were filled in by Klenow enzyme, (Boehringer Mannheim, Germany) and the ends were religated. Fill-in reactions described herein were conducted as directed by the manufacturer of the Klenow enzyme (Boehringer Mannheim, Germany). The resulting plasmid construct was designated #1074. This manipulation restored the SalI restriction site.

The coding region of the alkaline phosphatase gene was isolated from construct #1074 by restriction with XbaI and SalI and ligated into construct #1080 that had been cleaved with the same enzymes. This ligation resulted in an intermediate recombinant plasmid containing an AP gene that was out-of-frame with respect to the tk region. For production of an in-frame fusion, the intermediate recombinant plasmid containing the AP sequence was cleaved with XbaI and HindIII, the 5'-overhangs were filled-in and the ends were religated. This manipulation also restored the XbaI site. The resulting plasmid was designated construct #1112.

The HIV-1 promoter was isolated from plasmid pHIVSCAT, as described in Selby and Peterlin, *Cell* (1990) 62:769–776, by treatment with Asp718 and HindIII. The isolated fragment was ligated into plasmid Bluescript from Stratagene (La Jolla, Calif.), that had been cleaved with the same enzymes. The resulting plasmid was designated construct #1075. The particular HIV-1 promoter in pHIVSCAT contains several point mutations that have been introduced to create restriction enzyme recognition sites. Comparison of the mutant promoter in pHIVSCAT with the wild-type HIV-1 promoter did not show any significant differences in activity. Part of the sequence of the mutant HIV-1 promoter of construct #1152 is represented in SEQ ID No. 1. The HIV-1 promoter was isolated from construct #1075 by restriction with EcoRV and then ligated into plasmid pTZ18U from Pharmacia (Piscataway, NJ), that had been cleaved with SmaI. The resulting plasmid was designated construct #1149.

To generate the final collision construct of this example, the HIV-1 promoter was isolated from construct #1149 by restriction with SalI and Asp718 and ligated into construct #1112 that was cleaved with the same enzymes. The resulting plasmid was designated construct #1152, the collision construct, the promoter sequence of which is represented in SEQ ID No. 1.

In the collision construct, construct #1152, the direction of transcription from the hCMV and that from the HIV-1 promoter were in opposite directions. The distance between the end of the AP coding region, as defined by the stop codon TAA, and the start of transcription in the HIV-1 promoter, as defined by +1 of the promoter sequence was about 213 nucleotides.

EXAMPLE 2

HIV Tat Protein Dependent Reduction of Alkaline Phosphatase Activity

HeLa cells were transiently transfected with the following: (1) 1 µg of plasmid #1152, the collision construct, and (2) various amounts of plasmid pSV7fd/TAT: 0 µg, 0.1 µg, 0.3 µg, 0.5 µg, and 1.5 µg, respectively. Plasmid pSV7fd/TAT is herein referred to as the Tat expression plasmid, and its construction is described below. The amount of DNA in each transfection assay was kept constant by adding Tat-inactive plasmid, the construction of which is also described below. Results are shown in FIG. 1. For transient transfection of HeLa cells described herein, lipofectamine (purchased from BRL, Gaithersburg, Md.) was used in accordance to the manufacturers' instructions. For transfections hereafter, except as expressly provided otherwise, 1 µg of the collision construct was used together with either 0.5 µg of Tat expression plasmid (pSV7fd/TAT) and/or 0.5 µg of Tat-Inactive plasmid. After approximately 8 hours, the cells were washed and incubated in fresh DME medium, supplemented with 10% fetal calf serum. About 16–20 hours after transfection, aliquots of the supernatant were analyzed for alkaline phosphatase activity according to the manufacturers' conditions (Clontech, Palo Alto, Calif.).

The Tat expression plasmid and the Tat-Inactive plasmid were constructed or used as follows. Plasmid pSv7fd/TAT was obtained from Peterlin at University of California at San Francisco and was constructed and used as described in Selby and Peterlin, *Cell* (1990) 62:769–776. Plasmid pSV7fd/TAT contains the coding region for the transcriptional activator Tat from HIV-1. In this plasmid, Tat expression is under control of the SV40 early promoter. Inactive Tat expression plasmid was generated by restriction of plasmid pSV7fd/TAT with XbaI. The DNA ends were filled-in and the plasmid religated. This procedure generated a frame shift mutant that resulted in a premature stop codon and no functional Tat protein expression. The resulting construct is referred to as Tat-inactive plasmid, and was used herein to keep the total amount of DNA in each transfection constant.

FIG. 1 shows a reduction of AP activity that was dependent on the amount of Tat expression plasmid added. Over the range of 0 to 2 µg of Tat expression plasmid, reporter gene activity decreased from about 100% to about 25%, resulting in about 75% inhibition at the highest level tested. Reporter activity was about 40% when Tat was present at a level of between about 0.3 to 0.5 µg of Tat expression vector. At this level, there is almost no nonspecific effect of Tat protein on CMV promoter activity.

EXAMPLE 3

Study of the Dependence of TAR on Tat for Reduction in AP Activity Using Deletion Constructs Derived from Construct #1152

To examine the dependence of the presence of the TAR sequence in the HIV-1 promoter for the observed Tat-dependent reduction in AP activity in the previous example, the following deletions were introduced into construct #1152: (1) deletion of a major portion of the TAR sequence, construct #1161; (2) deletion of the entire TAR sequence, construct #1225; (3) deletion of the entire TAR sequence and the TATA box, construct #1162; and (4) deletion of the entire TAR sequence, the TATA box, and the three Sp1 binding sites, construct #1163.

Construct #1152 was restricted with BglII and BamHI and the ends religated. The resulting plasmid represents construct #1161. This deletion removes about 36 nucleotides of the TAR sequence.

Complete removal of the TAR sequence was obtained by deleting nucleotides from position −14 to +59, by PCR using DNA of construct #1152 as template and primer #613 (5'-GCGAAGCTTTGCAGCTGCTTATATGCAGCA-3') and reverse primer, purchased from New England Biolabs, Beverly, Mass. The underlined sequence represents nucleotides −35 to −13 of the HIV-1 promoter beginning with HindIII restriction site; the non-underlined portion includes the HindIII restriction site that begins after the nucleotides GCG at the 5'-end. The resulting DNA fragment was digested with HindIII and Asp718 and religated into construct #1152 cleaved with the same enzymes. This manipulation also removed the start of transcription and generated construct #1225.

A third deletion construct was prepared from construct #1152 by restriction with XbaI and religation. The resulting plasmid is designated construct #1162. This deletion removes the complete TAR sequence and the region containing the TATA box sequence.

A fourth deletion construct was prepared from construct #1152 by restriction with SmaI and BamHI and the ends religated. The resulting plasmid is designated construct #1163. This deletion removes the complete TAR sequence, the TATA box sequence and the three Sp1 binding-site sequences.

Figure 2:
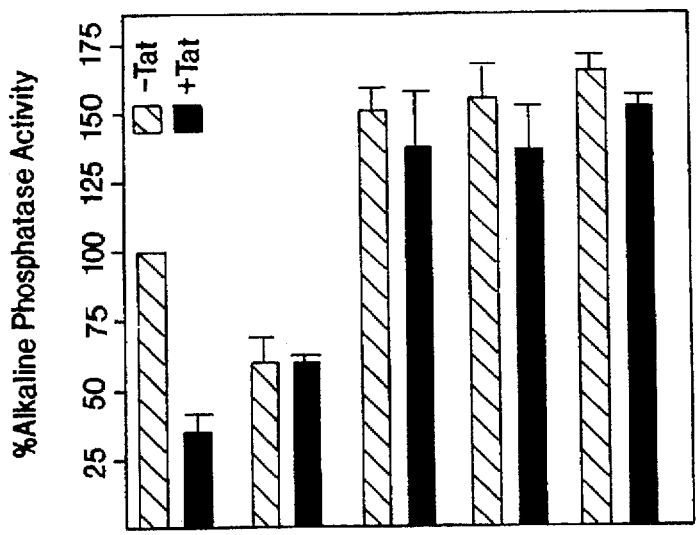
FIG. 2 is a schematic representation of five different collision constructs, designated as #1152, #1161, #1225, #1162, and #1163, and the reporter gene signals in percent alkaline phosphatase activity, generated by expression of 1 µg DNA each, respectively, and determined in the presence of 0.5 µg of Tat protein expression plasmid ("+Tat") or 0.5 µg inactive Tat protein expression plasmid ("-Tat") in HeLa cells.
Figure 2:
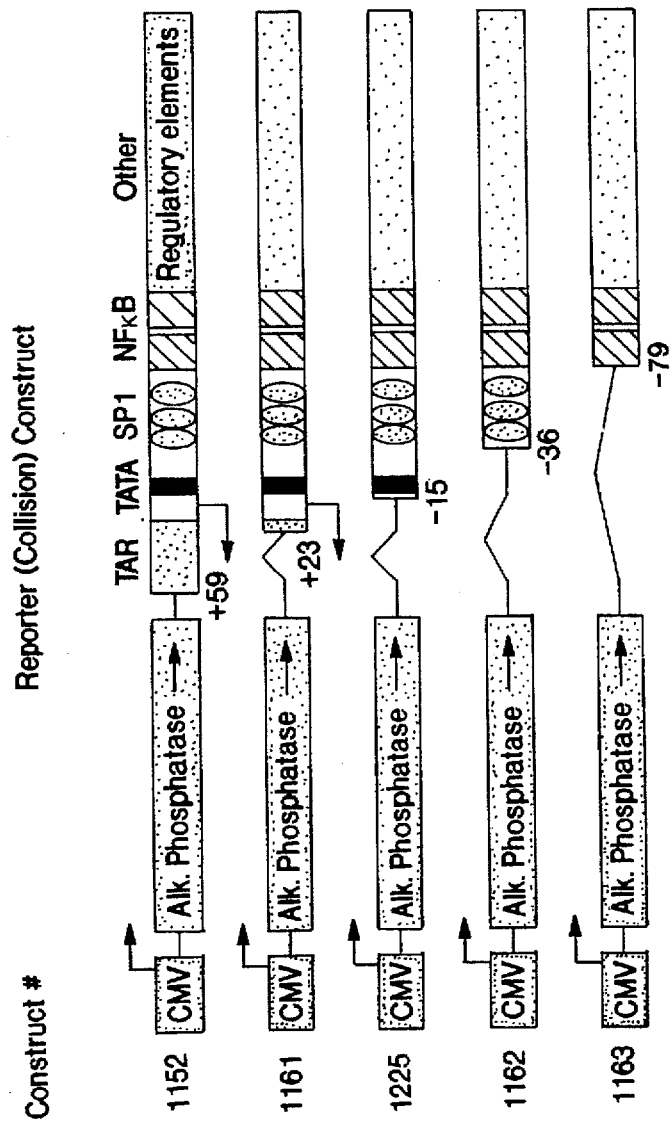

FIG. 2 shows the results of measuring the specific reduction of alkaline phosphatase expression in the presence of 0.5 µg HIV-1 Tat protein expression plasmid in the deletion constructs #1161, #1225, #1162 and #1163, as compared with construct #1152. For construct #1152, in the absence of Tat, activity of the AP gene was set to 100%. In the presence of Tat, activity of the AP gene was reduced to 36% ±7%. Thus, in the presence of Tat, expression of AP was reduced by about 64%. For construct #1161, in which most the TAR sequence was deleted, expression of the AP gene in the absence of Tat was about 55%. Addition of Tat only reduced AP gene expression to about 53%, indicating that inhibition of reporter gene activity by Tat protein is TAR sequence dependent. Construct #1225, containing a deletion in the TAR sequence, produced about 150% AP gene activity in the absence of Tat, and about 140% AP gene activity in the presence of Tat. Construct #1162, containing a deletion in the TAR sequence and in the TATA box, produced about 150% AP gene expression in the absence of Tat protein, and about 153% AP gene expression in the presence of Tat. Construct #1163, containing deletions in the TAR sequence, the TATA sequence and the Sp1 binding sites, generated a still higher level of AP gene expression of about 160% in the absence of Tat, and about 150% in the presence of Tat. These results demonstrate the requirement for a functional TAR sequence and a TATA box sequence for activation of the HIV-1 promoter. In addition, significant upregulation of HIV-1 promoter activity by Tat protein requires a functional TAR sequence.

EXAMPLE 4

Effect of Various Deletions of the HIV-1 Promoter on Transcriptional Activation and Construction of TAT-Inactive Plasmid Other constructs were made to test the effect of deletion of portions of a promoter region on transcriptional activation, using the AP gene as the reporter gene. Construct #1085 was made using the mutant HIV-1 promoter as described in Example 3, as an Asp718/HindIII DNA fragment isolated from pHIVSTAT and ligated into plasmid pSEAP-Basic (Clontech, Palo Alto, Calif.) that was cleaved with the same enzymes. This operation linked the HIV-1 promoter to the AP gene. Constructs #1166, #1213, #1167 and #1168 were made by isolating the HIV-1 promoter deletion constructs from construct #1161, #1215, #1162 and #1163, described above, and ligating them as Asp718/HindIII fragments into plasmid pSEAP-Basic. Thus, construct #1085 contains the entire HIV-1 promoter. Construct #1166 lacks about 36 nucleotides of the TAR sequence. Construct #1213 lacks all of the TAR sequence and nucleotides comprising the original start of transcription. Construct #1167 lacks the TAR sequence and the TATA box. Construct #1168 lacks the TAR sequence, the TATA box, and the three Sp1 binding sites. HeLa cells were transiently transfected with the latter constructs as described before and AP gene expression was observed as described before.

Figure 3:
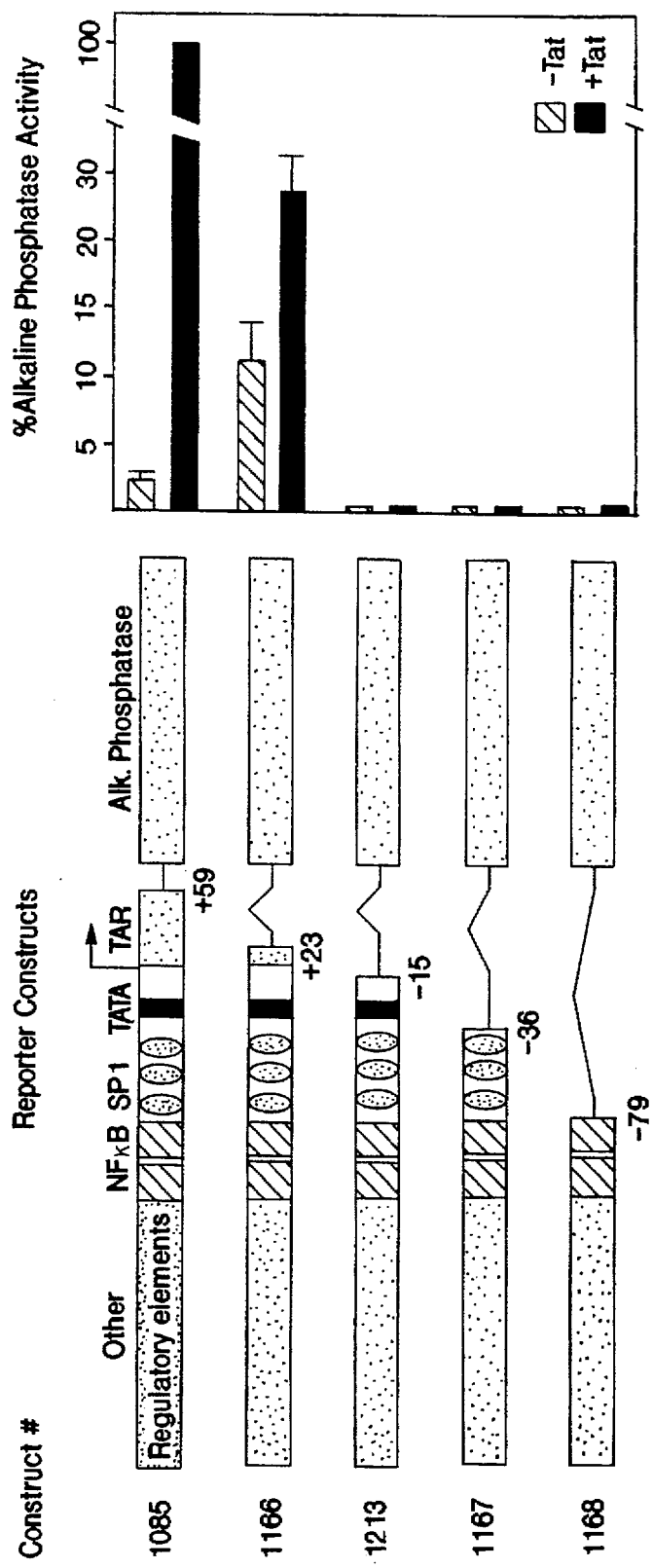
FIG. 3 is a schematic representation of five different reporter constructs, designated as #1085, #1166, #1213, #1167, and #1168, and the reporter gene signals, indicated as percent alkaline phosphatase activity, generated by expression of 1 µg of each, respectively, in the presence of 0.5 µg Tat protein expression plasmid ("+Tat") or 0.5 µg inactive Tat protein expression plasmid ("-Tag") in HeLa cells. The alkaline phosphatase activity measured with construct #1085 in the presence of active Tat protein expression plasmid was set to 100%.

FIG. 3 shows that in the absence of Tat, the full-length HIV-1 promoter in construct #1085, containing the TAR sequence, was unable to induce significant expression of the AP gene, resulting in about 2% AP gene activity. In the presence of 0.5 µg protein expression plasmid Tat, construct #1085 activated AP gene expression. The AP gene activity produced by construct #1085 was set to 100%. Thus, in the presence of Tat, there was approximately, a 50-fold activation. Deletion construct #1166 that lacked most of the TAR sequence showed only about 2% AP activity in the presence of Tat protein. However, in the absence of Tat protein, the truncated HIV-1 promoter produced about 12% AP activity. Deletion constructs #1213, #1162 and #1163 showed no basal and also no Tat-inducible promoter activity.

EXAMPLE 5

Constructs to Study the Effect of Spacing on the Function of the Collision Construct Constructs having varying distances or spacer regions between the first and second promoters or between the second promoter and reporter gene were made to study the effect of spacing on the function of the collision construct.

The various collision constructs made contained spacer regions of 21 nucleotides (construct #1190), 94 nucleotides (construct #1181), 153 nucleotides (construct #1187), 406 nucleotides (construct #1188), 556 nucleotides (construct #1189) and 2047 nucleotides (construct #1159), positioned between the 3' end of the AP coding sequence, as defined by the stop codon, and the end of the TAR sequence at +59 nucleotide in the HIV-1 promoter, with +1 nucleotide as the start of transcription. Those constructs were made as follows: Construct #1190 was made by restriction digest of construct #1152 with HpaI and HindIII and religation. This manipulation changed the stop codon from TAA to TGA. Construct #1181 was made by restriction digest of construct #1152 with SalI and HindIII and religation. Constructs #1187, #1188 and #1189, respectively, were made by insertion of parts of the PEBP2α coding region, as described in Ogawa et al. (1993) *Proc. Natl. Acad. Sci. USA* 90:6859–6863, as a SacI/HindIII DNA fragment, an Asp718/HindIII DNA fragment or a NcoI/HindIII DNA fragment, respectively, into construct #1152 cleaved with SalI which was blunt-ended and HindIII. Construct #1159 was made by insertion of the luciferase gene isolated from plasmid pT3/T7-Luc (Clontech, Palo Alto, Calif.) as a SalI/Asp718 fragment into construct #1152 cleaved with the same enzymes. Results are shown in FIG. 4.

Figure 4:
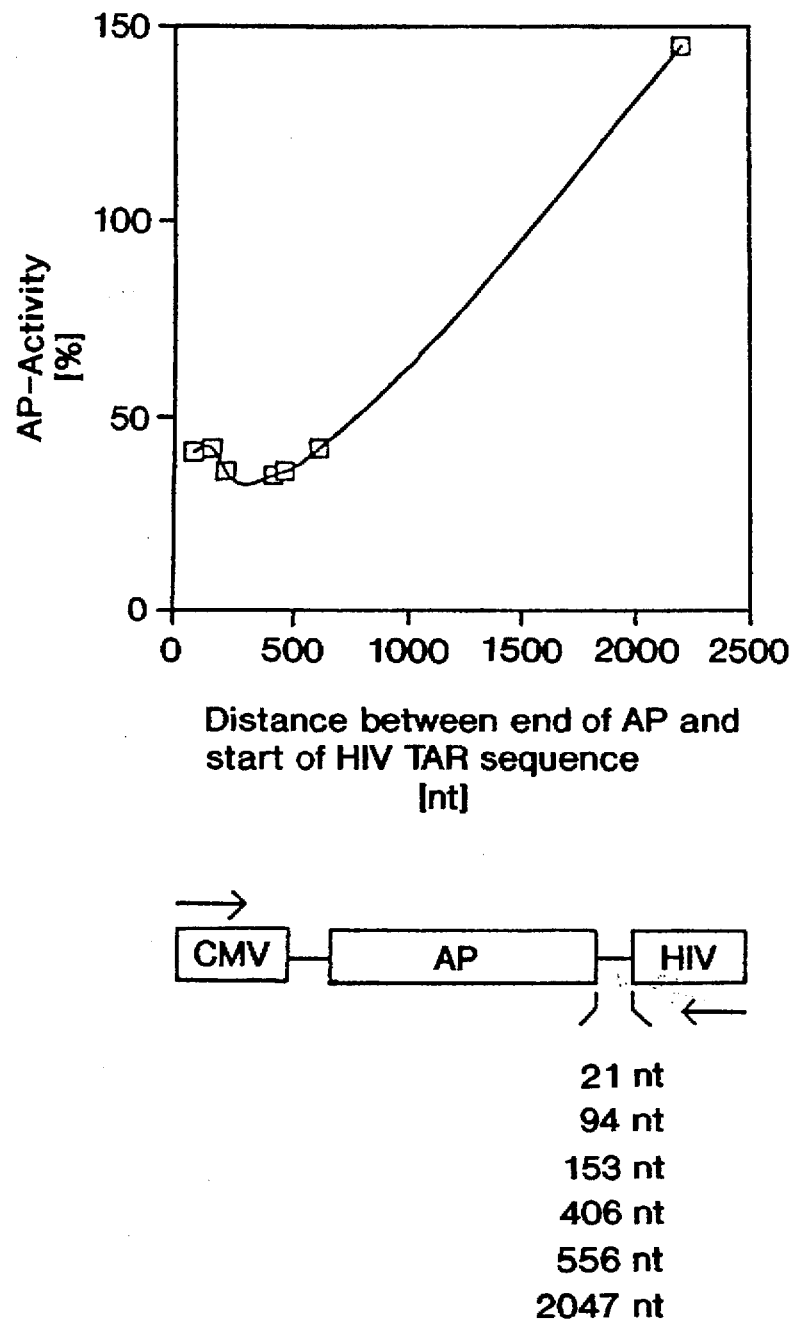
FIG. 4 is a schematic representation of different collision constructs containing spacer regions of about 21, 94, 153, 406, 556 and 2047 nucleotides, positioned between the 3' end of the AP coding sequence, as defined by the stop codon TAA, or TGA in construct with a spacer of 21 nucleotides, and the end of the TAR sequence at nucleotide +59 in the HIV-1 promoter, with +1 nucleotide as the start of transcription.

FIG. 4 illustrates that collision, inhibition, or AP expression is dependent on the spacing between the HIV-1LTR and the reporter gene, or alternatively, on the spacing between the first promoter and the second promoter. In the presence of 0.5 μg of Tat expression plasmid, AP activity in constructs with spacing from about 21 nucleotides to about 556 nucleotides is between 40% and 46%, and thereafter, as the spacing increased to about 2047 nucleotides, the alkaline phosphatase activity increased, indicating a certain space requirement for collision. Transient transfections were done using 1 μg of collision construct DNA and 0.5 μg of either active or inactive Tat expression plasmid. These results illustrate that collision is dependent on the spacing between the HIV-1 LTR and the first regulatory sequence that included the reporter gene.

EXAMPLE 6

HeLa Cells Stably-Transfected with Tat Protein Expression Plasmid

HeLa cells were transfected with 10 μg of either active Tat expression plasmid or with Tat-inactive plasmid together with 1 μg of plasmid pSVNeo (purchased from Clontech, Palo Alto, Calif.) for selection by electroporation using a BioRad Gene Pulser (Purchased from BioRad, Hercules, Calif.). Electroporation was conducted in accordance with the manufacturer's instructions. For example, the conditions for electroporation are 1000 μF and 300 volts at room temperature in a final volume of 500 μl medium containing 10% fetal calf serum, and 50 μg/ml each of penicillin and streptomycin. Stable Tat expression colonies were identified by resistance to 400 μg/ml gentamicin (purchased from GIBCO BRL) after about 10 to 14 days. Stable colonies were picked, amplified, and analyzed for Tat protein expression by transfection with construct #1085, the plasmid with an HIV-1 promoter linked to the AP reporter gene. Positive Tat-expressing cell lines were identified by measuring alkaline phosphatase activity, according to directions described by the manufacturer of pSVNeo (Clontech, Palo Alto, Calif.).

EXAMPLE 7

Assay to Screen for Inhibitors of Transcriptional Activation

The following assay is designed to screen for inhibitors of the Tat protein, the Tat/TAR interaction or any other HIV-1 promoter target. The inhibition sought is identified by significant inhibition of long terminal repeat (LTR) activity. Cell lines are stably transfected as described in Example 6 above with the collision construct #1152 and the Tat plasmid. Those stably transfected cell lines that produce a steady-state alkaline phosphatase activity of about ~30% to 40% compared to control HeLa cells stably transfected with only the collision construct are selected for screening. Screening for inhibitors is conducted as follows: inhibitors are introduced into the culture medium and, after about 16 to 20 hours, the supernatant is analyzed for alkaline phosphatase activity, as described in Example 6. Using a 96-well assay plate, for example, 12 different inhibitors, at 8 different concentrations, are tested simultaneously. Those inhibitors that produce an increase in alkaline phosphatase activity are further characterized by transient transfection experiments. Transient transfections are conducted as described in Example 2. For example, HeLa cells are transiently transfected with construct #1152 and a controlled amount of Tat plasmid in the presence of an inhibitor. The inhibitor is then tested for dose responsiveness to Tat by titrating the inhibitor or the Tat expression plasmid. Separate transient transfection assays are repeated for each inhibitor selected by the screening process described above.

EXAMPLE 8

Constructs Including TAR Decoys

To prove the functionality of the collision construct in identifying inhibitors of HIV-1 transcription by an increase in AP reporter gene activity, we constructed vectors containing multimerized TAR sequences (a schematic of which is indicated in FIG. 6). Overexpression of TAR-containing sequences, referred to as TAR decoys have proved sufficient at inhibiting HIV-1 promoter activity by squelching Tat-mediated transactivation, as described in Sullenger et al, *Cell* 63: 601–608 (1990) and Graham and Maio, *Proc. Nat'l Acad Sci USA* 87:5817–5821 (1991). The ability of Tar decoys to block HIV-1 transcription was previously analyzed with an HIV-AP construct in which the reporter gene was placed under the regulatory control of the HIV-1 promoter, as schematically represented in FIG. 6a. Transfection of the HIV-AP plasmid together with a Tat expression vector into HeLa cells showed approximately a 45-fold stimulation of reporter gene expression relative to the level detected in the absence of Tat. Addition of the TAR decoys almost completely abolished the transactivation function of Tat. Next, the ability of the TAR decoys to inhibit HIV-1 transcription in the context of the collision construct, as represented schematically in FIG. 5b. The results showed that the addition of TAR decoys blocked the potential of Tat to repress reporter gene expression by counter-transcription. At high TAR decoy concentrations, AP activity was even higher than the level detected in the absence of Tat, as shown in lanes 4 and 5 of FIG. 5b. These data suggest that the TAR decoys sequester not only Tat but also other cellular factors that bind to the TAR sequence. This result is further supported by the result schematically depicted in a portion of FIG. 1 that indicated that AP values detected with a ΔTAR construct are similar to the values obtained with the wild type collision construct in the presence of the TAR decoys.

The plasmid pBJ-TAR8 was constructed by insertion of multimerized TAR sequences isolated from pHIVSCAT with XbaI and HindIII restriction enzymes (nucleotides –40 to +59) downstream of the Sra promoter in pBJ, as described in Takebe et al *Mol. Cell. Biol.* 8:466–472 (1988). As a control plasmid, the leptin gene, as described in Giese et al Embo J. 12:4667–4676 (1993) with a similar size compared to the TAR sequences was inserted into the pBJ vector.

c) a second regulatory sequence that comprises a second promoter;

wherein the first promoter is different from the second promoter, and direction of transcription under the first promoter is opposite to direction of transcription under the second regulatory sequence, and wherein regulation of the second promoter alters expression of the reporter gene.

2. The collision construct of claim 1, wherein the second promoter comprises a first response element that specifically binds to a first binding protein to form a first binding pair; and formation of the first binding pair regulates the second promoter under transcription-regulating conditions.

3. The collision construct of claim 1, wherein the regulation of the second promoter is achieved by activation thereof.

4. The collision construct of claim 1, wherein the second promoter comprises a 5' terminus and a 3' terminus and the reporter gene is separated from 3' terminus of the second promoter by a distance of about 2047 nucleotides or less.

5. The collision construct of claim 4, wherein the distance is in a range selected from the group of ranges, in nucleotides, of about 1–50, 51–100, 101–150, 151–200, 201–300, 301–400, 401–500, 501–600, 601–1000, 1001–1500, and 1501–2047.

What is claimed is:

1. A collision construct comprising a nucleic acid molecule that comprises:

a) a first regulatory sequence that comprises a first promoter;

b) a reporter gene that is under transcriptional control of the first promoter; and 6. The collision construct of claim 4, wherein the distance is in a range selected from the group of ranges, in nucleotides, of about 1–20, 21–40, 41–60, 61–80, 81–100, 101–120, 121–140, 141–160, 161–250, 251–425, and 426–550.

7. The collision construct of claim 4, wherein the distance, in nucleotides, is selected from the group consisting of about 21, 94, 153, 406, 556 and 2047.

8. The collision construct of claim 1, wherein the first promoter is a minimal promoter.

9. The collision construct of claim 1, wherein one or both of the first and second promoters are each selected from the group consisting of promoters derived from a virus, a bacteriophage, a prokaryotic gene, and an eukaryotic gene.

10. The collision construct of claim 9, wherein the virus is selected from the group consisting of a retrovirus, a vaccinia virus, a herpes virus, a hepatitis virus, a papilloma virus, an adenovirus, and an adeno-associated virus.

11. The collision construct of claim 1, wherein the first promoter is selected from the group consisting of a $\lambda_{PL}$ promoter, a $\lambda_{PR}$ promoter, a prokaryotic ribosomal RNA P1/P2 promoter, a Rous Sarcoma Virus promoter, a Simian Virus 40 promoter, a simian immunodeficiency virus promoter, an albumin promoter, a lck promoter, and a fos promoter.

12. The collision construct of claim 9, wherein second promoter is a promoter derived from a virus and the virus is selected from the group consisting of a cytomegalovirus, a herpes simplex virus, a hepatitis virus, and a human immunodeficiency virus.

13. The collision construct of claim 9, wherein the second promoter is selected from the group consisting of a flt promoter, a CD4 promoter, and a β-3 promoter.

14. The collision construct of claim 1, wherein one or both of the first regulatory sequence and second regulatory sequence comprise a synthetic sequence.

15. The collision construct of claim 14, wherein the first regulatory sequence comprises a synthetic sequence and the synthetic sequence is selected from the group consisting of a multimeric Gal4 binding site linked to a minimal promoter and a LexA binding site linked to a minimal promoter.

16. The collision construct of claim 14, wherein the synthetic sequence comprises a TATA box.

17. The collision construct of claim 1, wherein the first promoter comprises a second response element that specifically binds to a second binding protein to form a second binding pair, wherein formation of the second binding pair regulates the first promoter under transcription-regulating conditions, and the second binding protein specifically binds to the first promoter.

18. The collision construct of claim 1, wherein the reporter gene is selected from the group consisting of genes encoding alkaline phosphatase, luciferase, chloramphenical acetyltransferase, β-galactosidase, β-glucuronidase, and green fluorescent protein.

19. The collision construct of claim 2, wherein the first response element is derived from a promoter or promoter/enhancer region of a gene selected from the group consisting of a viral gene, a bacteriophage gene, a prokaryotic gene, and an eukaryotic gene.

20. The collision construct of claim 17, wherein the second response element is derived from a promoter or promoter/enhancer region of a gene selected from the group consisting of a viral gene, a bacteriophage gene, a prokaryotic gene and an eukaryotic gene.

21. The collision construct of claim 2, wherein the first response element is selected from the group consisting of a transactivation response element ("TAR"), Rev response element ("RRE"), a NF-κB binding site, and a Sp1 binding site.

22. The collision construct of claim 17, wherein the second response element is selected from the group consisting of a transactivation response element ("TAR"), Rev response element ("RRE"), a NF-κB binding site, and a Sp1 binding site.

23. The collision construct of claim 2, wherein the first binding protein is selected from the group consisting of Tat, Rev, NF-κB, and Sp1.

24. The collision construct of claim 1, wherein the first promoter has a strength of transcription that is approximately the same as that of the second promoter upon activation.

25. A vector comprising the collision construct of claim 1, further comprising a nucleotide sequence that allows for expression of the collision construct in a host cell.

26. A host cell comprising the vector of claim 25.

27. The host cell of claim 26, wherein the host cell amplifies the collision construct or effecting the expression thereof.

28. The host cell of claim 26, wherein the cell is selected from the group consisting of a prokaryotic cell and an eukaryotic cell.

29. The host cell of claim 27, wherein the cell amplifies the collision construct and is a prokaryotic cell.

30. The host cell of claim 27, wherein the cell expressed the collision construct and is an eukaryotic cell.

31. A kit comprising the collision construct of claim 1, further comprising instructions for use thereof.

32. A kit comprising the vector of claim 25, further comprising instructions for use thereof.

33. A kit comprising the host cell of claim 26, further comprising instructions for use thereof.

34. A method for screening a candidate inhibitor for its ability to inhibit transcription under a target promoter comprising:

a) providing a cell that comprises the collision construct of claim 1, wherein the second promoter is the target promoter;

b) determining reporter gene signal in the presence and absence of the candidate inhibitor: and c) comparing reporter gene signals obtained to determine whether inhibition of transcription under the second promoter occurred in the presence of the candidate inhibitor, wherein, when the reporter gene signal is increased, the target promoter is inhibited.

35. The method of claim 34, wherein the target promoter is not endogenous to the cell.

36. The method of claim 34, wherein the target promoter is endogenous to the cell.

37. A method for screening a candidate inhibitor for its ability to inhibit binding between a target binding protein and a target response element comprising:

a) providing a cell that comprises the collision construct of claim 2, wherein the first binding protein is the target binding protein and the first response element is the target response element;

b) providing a baseline reporter gene signal in the absence or presence of the target binding protein;

c) determining reporter gene signal in the presence and absence of the candidate inhibitor; and d) comparing reporter gene signals obtained, wherein when the reporter gene signal is increased, the binding between a target binding protein and a target response element is inhibited.

38. The method of claim 37, wherein the target response element is not endogenous to the cell.

39. The method of claim 37, wherein the target response element is endogenous to the cell.

40. The method of claim 37, wherein the target binding protein is provided by a process selected from the group consisting of:

a) introducing into the cell a nucleotide sequence that encodes the target binding protein;
b) allowing a cell which produces the target binding protein constitutively to produce the target binding protein; and
c) adding the target binding protein to the cell.

41. A method for identification of an inhibitor of transcription under a target promoter comprising:
a) providing a cell that comprises the collision construct of claim 1, wherein the second promoter is the target promoter;
b) determining reporter gene signal in the presence and absence of a panel of candidate inhibitors;
c) comparing reporter gene signals obtained to determine if inhibition of target promoter activity has occurred in the use of any one of the panel of candidate inhibitors, wherein when the reporter gene signal is increased, the transcription of the target promoter is inhibited.

42. A method for making a reporter collision construct, comprising:
a) providing a first regulatory sequence that comprises a first promoter, a reporter gene that is capable of providing a detectable signal upon transcription and translation, and a second regulatory sequence that comprises a second promoter; and
b) linking the first regulatory sequence, the reporter gene, and the second regulatory sequence together to produce the collision construct of claim 1.

43. A method for production of a collision construct, comprising culturing the host cell of claim 33.

44. A collision construct produced by a process comprising replicating the collision construct of claim 1 in a prokaryotic or eukaryotic cell.

45. The collision construct of claim 44, wherein the eukaryotic cell is selected from the group consisting of a mammalian cell, an insect cell, a yeast cell, and an avian cell.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
       ( A ) LENGTH: 525 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:1:

```
CTGCAGGTCG  ACTCTAGAGG  ATCCCCATCA  AGCTTTATTG  AGGCTTAAGC  AGTGGGTTCC    60

CTAGTTAGCC  AGAGAGCTCC  CAGGCTCAGA  TCTGGTCTAA  CCAGAGAGAC  CCAGTGCATG   120

CAAAAAGCAG  CTGCTTATAT  GCAGCATCTA  GAGGGCACGC  CACTCCCAG   TCCCGCCAG    180

GCCACGCCTC  CCGGGAAAGT  CCCCAGCGGA  AAGTCCCTTG  GAGAAAGCTC  GATGTCAGCA   240

GTCTTTGTAG  TACTCCGGAT  GCAGCTCTCG  GGCCATGTGA  TGAAATGCTA  GTTTGCTGTC   300

AAACCTCCAC  ACTAACACTT  CTTTCTCCGC  GTCCTCCATC  CCATGCAGGC  TCATAGGGTG   360

TAACAAGCTG  TTGTTCTCTC  CTTCATTGGC  CTCTTCTACC  TTCTCTGGCT  CAACTGGTAC   420

TAGCTTGAAG  CACCATCCAA  AGGTCAGTGG  ATGGGTACCG  AGCTCGAATT  CCCTATAGTG   480

AGTCGTATTA  AATTCGTAAT  CATCAGCATA  ATTTAAGCAT  TAGTG                    525
```